US00PP36004P2

(12) United States Plant Patent
Hansen

(10) Patent No.: US PP36,004 P2
(45) Date of Patent: Jul. 9, 2024

(54) ***PENSTEMON* PLANT NAMED 'PINK PEARLS'**

(50) Latin Name: ***Penstemon* hybrid**
Varietal Denomination: Pink Pearls

(71) Applicant: Hans A Hansen, Zeeland, MI (US)

(72) Inventor: Hans A Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 18/445,662

(22) Filed: Dec. 15, 2023

(51) Int. Cl.
*A01H 6/68* (2018.01)
*A01H 5/02* (2018.01)

(52) U.S. Cl.
USPC ..... Plt./465

(58) Field of Classification Search
USPC ..... Plt./263.1, 465
See application file for complete search history.

*Primary Examiner* — Karen M Redden

(57) ABSTRACT

The new and distinct cultivar of *Penstemon* plant named 'Pink Pearls' with strictly upright, tightly-compact strong stems, and numerous, medium, rosy-colored flowers for about four weeks beginning in early summer and repeating in late summer if deadheaded. The lanceolate foliage is bluish-green, the plant is winter hardy to at least USDA zone 4, long-lived, and persistent in the landscape. The new plant is useful in the landscape as a specimen plant, en masse, or container plant, and attractive to hummingbirds.

1 Drawing Sheet

Botanical classification: *Penstemon* hybrid.
Variety denomination: 'Pink Pearls'.

STATEMENT REGARDING PRIOR DISCLOSURES UNDER 37 CFR 1.77(B)(6)

The first offer for sale was on Jan. 9, 2023, and the first sale was made by Walters Gardens, Inc. on Aug. 21, 2023, to N. Casertano Greenhouses and Farms, Inc. Walters Gardens, Inc. obtained the new plant and all information relating thereto, from the inventor. No plants of *Penstemon* 'Pink Pearls' have been sold anywhere in the world by any name nor has any disclosure of the new plant been made more than one year prior to the filing date of this application, and such sale or disclosure within one year was either derived directly or indirectly from the inventor.

BACKGROUND OF THE INVENTION

The present invention relates to a new and distinct plant of Beardtongue, botanically known as *Penstemon* 'Pink Pearls' and will be referred to hereinafter also by its cultivar name 'Pink Pearls' and as the new plant. The new plant cultivar of Beardtongue is a hardy herbaceous perennial grown for landscape use.

*Penstemon* 'Pink Pearls' is a single seedling selection derived from a cross between the proprietary unreleased hybrid known only as 13-7-2 (not patented) as the female parent and the proprietary unreleased hybrid known only as 13-8-9 (not patented) as the male parent on Jun. 9, 2016, at a wholesale perennial nursery in Zeeland, Michigan. Among the goals of the hybridizing program are to produce good garden plants with more persistent and longer-lived plants. The seed was collected in the fall of 2016. All subsequent evaluations were performed in a full-sun trial garden at the same nursery with loamy sand soil and irrigation and fertilizer as required. The individual seedling was assigned the breeder code 16-9-2 while being selected for further trials during the summer of 2018. The new plant was propagated by basal shoot cuttings at the same nursery in Zeeland, MI, and the original plant and the cuttings were evaluated over the next four years until final approval for introduction in the summer of 2021. The resultant asexually propagated cuttings have been stable and identical to the original plant in successive asexual propagations.

SUMMARY OF THE INVENTION

*Penstemon* 'Pink Pearls' differs from its parents as well as all other hardy Beardtongue known to the inventor in a combination of traits. The following characteristics in combination distinguish 'Pink Pearls' from all other Beardtongue plants known to the inventor:

1. Round mounded growth with tightly-compact strong upright stems;
2. Glaucous lanceolate foliage developing and maintaining a bluish-green coloration in high light intensity;
3. Flowering with numerous medium rosy-colored flowers for four weeks beginning early summer in Michigan and repeating in late summer if deadheaded;
4. Winter hardy to at least USDA zone 4.
5. Long-lived and persistent in the landscape.

The nearest comparison cultivars are: 'TNPENHPI' U.S. Plant Pat. No. 31,500, 'P008S' (aka. RED ROCKS®) (not patented), 'Rosy Blush' (not patented), 'Dopensprispin' U.S. Plant Pat. No. 33,061, 'Carolyn's Hope' (not patented), and 'Pinacolada Rosey' (not patented).

'TNPENHPI' has a taller habit, the flowers are lighter pink with a white inner corolla tube, and the labia lobes are flatter. 'P008S' has a similar height, but the flowers are broader with flatter labia lobes, and the inner corolla tube is nearly white. 'Rosy Blush' has a taller habit, the flower is broader, and the inner corolla tube is nearly pure white. 'Dopensprispin' has a taller habit and the flower is lighter pink. 'Carolyn's Hope' has a taller habit, the flowers are lighter rose, and the flowering is less dense. 'Pinacolada Rosey' has a similar height, but the flowers are lighter pink.

The female or seed parent, 13-7-2 has more reddish flowers. The male or pollen parent, 13-8-9, has a shorter and is more compact in habit.

BRIEF DESCRIPTION OF THE DRAWINGS

The photographs of the new plant demonstrate the overall appearance of the plant, including the unique traits. The colors are as accurate as reasonably possible with color reproductions. Ambient light spectrum, source, temperature, and direction may cause the appearance of minor variations in color. The plants used in the photograph are two-year-old plants grown in full sun field in loamy sand soil in trial gardens of a nursery in Zeeland, Michigan.

DETAILED BOTANICAL DESCRIPTION

Figure 1:
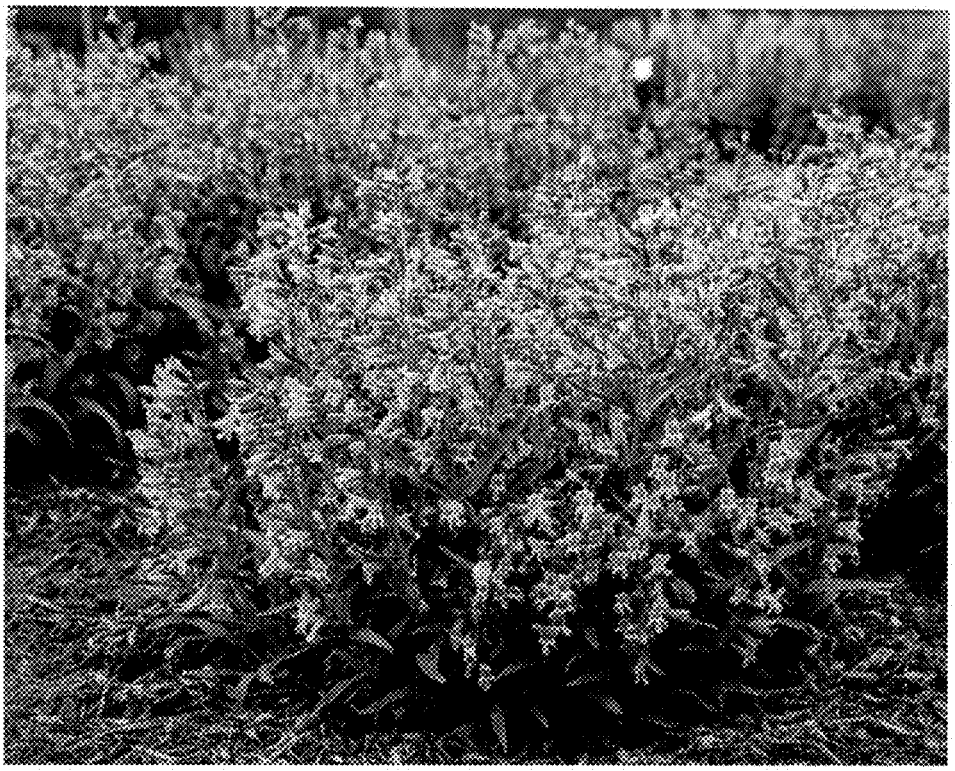
FIG. 1 shows the new plant in the foreground of a display garden in peak flower with 'Rose Rhinestones' in the background for comparison.
Figure 2:
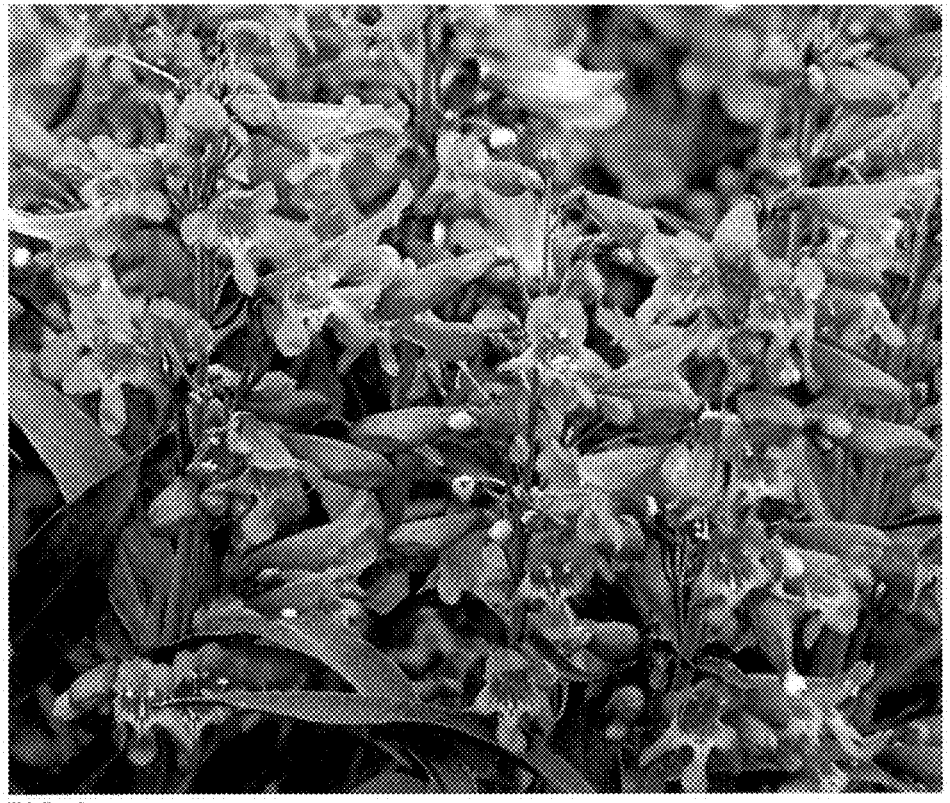
FIG. 2 shows a close-up of the flowers and buds.

The following is a detailed description of *Penstemon* 'Pink Pearls' as observed and compared to other cultivars for two years in trial gardens and production fields at a nursery in Zeeland, Michigan. The following description is of a two-year-old plant growing in a full-sun display garden in Zeeland, MI with limited supplemental fertilizer and irrigation as needed and without any pinching or plant growth regulators. The new plant has not been observed under all possible environments, and the phenotype may vary slightly with different environmental conditions, such as temperature, light, fertility, moisture, and maturity levels, but without any change in the genotype. The color descriptions are in accordance with the 2015 edition of The R.H.S. Colour Chart of The Royal Horticultural Society, London, England, except where common dictionary color terms are used.

Parentage: The female (seed) parent is 13-7-2 and the male (pollen) parent is 13-8-9;

Plant habit: Herbaceous winter-hardy, perennial with upright rigid stems emerging from the base in the spring; up to about 15 stems per plant; flowering in branched panicle;

Plant size: About 30 cm in height, average stem 25 cm tall, and about 20 cm in width about 10 cm above soil;

Root description: Fibrous, well-branched, developing to about 1 mm thick; color between RHS 161A and RHS 161B;

Propagation: Shoot-tip cuttings; root initiation occurs in about 14 days at a temperature of 22° C.;

Growth rate: Moderately vigorous;

Crop time: About 12 to 14 weeks to finish in a 3.8-liter pot from a rooted plug;

Stem description: Terete; oppositely branched in the distal region; glabrous; glaucous; to about 30 cm long and about 4 mm diameter at base;

Stem color: Between RHS 138A and RHS N138B;

Node: About 5 per stem below flowers, average internode length about 2.8 cm, larger toward flowers;

Internode color: Same as surrounding stem;

Foliage description: Simple; lanceolate; glabrous and slightly glaucous adaxial and abaxial; sessile with attenuate base; margin entire; fragrance not detected;

Leaf size: Basal leaves to about 87 mm long and about 16 mm wide;

Leaf color: Young expanding adaxial and abaxial between RHS N138A and RHS 132A; mature adaxial between RHS N138A and RHS 133B, abaxial nearest RHS N138C;

Leaf venation: Pinnate;

Petiole: Absent;

Vein color: Adaxial midrib nearest RHS 146D in basal portion and between RHS N138A and RHS 133B, abaxial midrib nearest RHS 145A; adaxial and abaxial secondary veins same as surrounding leaf tissue;

Inflorescence: Panicle; to about 16 cm long and about 7 cm across; with up to 45 flowers per inflorescence;

Pedicel: Cylindrical; glabrous, lustrous; size in length, between 5 and 10 mm long, and 1.0 mm diameter;

Pedicel color: Nearest RHS 146D;

Peduncle: Branched panicle with up to eight branches; smooth, glabrous; main stems vertical; to about 30 cm tall and 4 mm diameter base flowering in upper 16 cm; to about 45 flowers per stem and 8 flowers per branch;

Peduncle color: Between RHS 146D and RHS 147C;

Flower buds about one day prior to opening: About 28 mm long, about 7 mm wide distally, and 3 mm diameter near the base; clavate; rounded apex; basal 3 mm of corolla tube narrowed to about 3 mm diameter, with rounded base;

Bud color: Dorsal labium proximally nearest RHS 71A, distally between RHS 53C and RHS 51A, ventrally nearest RHS 53C with veins of nearest RHS 71A;

Flowering season: Beginning in early June to early July and flowering for about five weeks, repeating if deadheaded;

Flowers: Zygomorphic; perfect; complete; bilabiate with upper and lower lip gamopetalous in about basal 22 mm; about 36 mm long and about 15 mm across and 15 mm tall at the face; face flat when first open becoming reflexed and longitudinally folded in ventral lobes; lasting about five to seven days;

Flower attitude: Mostly outward;

Flower fragrance: None detected;

Corolla: Bilabiate; ventral petal with three lobes; dorsal petal with two lobes; glabrous abaxial; glabrous adaxial dorsal petal and fused tube portion, except pubescent on an adaxial ventral petal in the distal portion near mouth; dorsal petal lobes about 3 mm long and 3 mm across at fusion with rounded apices; two ventral lobes side lobes about 3 mm wide at division; just beyond midpoint between fusion and apex, center ventral lobe about 6 mm long and 4 mm across; all lobes with rounded apices and entire margins; corolla tube about 22 mm long, 6 mm wide and 6 mm across at fusion and 3 mm diameter at base;

Corolla color: Ventral and dorsal adaxial lobes between RHS 63C and RHS 63D, basal 4 mm of corolla tube between RHS 145D and RHS 155C, next 4 mm between RHS 67A and RHS 64B, middle dorsal portion nearest RHS 65D and middle ventral portion nearest RHS 64C striated with nearest RHS 65D; abaxial basal 4 mm between RHS 145D and RHS 155C, next 4 mm between RHS 67A and RHS 64B, distal 24 mm nearest RHS 63C;

Gynoecium: Single; superior; persistent after corolla drops; about 32 mm long;

*Style*.—Cylindrical; glabrous; arcuate slightly downwardly distally; about 26 mm long and about 0.5 mm diameter; color nearest RHS NN155B developing a light blush of nearest RHS 71A after corolla drop.

*Stigma*.—Semi-globose, to about 0.5 mm diameter; color nearest RHS NN155A.

*Ovary*.—Oblong conical; with truncate base and acute apex; about 6 mm long and 2 mm across at base; color between RHS 145A and RHS 146D.

Androecium: Four; didynamous; slightly arcuate;

*Filaments*.—Longer set about 27 mm long and adnate inner corolla in basal 13 mm, shorter set about 21 mm long adnate inner corolla in basal 4 mm, about 1 mm in diameter; color distal portion nearest RHS NN155B, and basal 4 mm between RHS 145D and RHS 155C.

*Anther*.—Elliptic; basifixed; longitudinal; bent at filament attachment; about 4 mm long and 1.5 mm across; color nearest RHS 11C.

*Staminode*.—Single; cylindrical; about 19 mm long and 0.5 mm diameter; adnate to inner corolla tube in basal 8 mm.

*Staminode color*.—Basal 4 mm between RHS 145D and RHS 155C, distally nearest RHS NN155B.

*Pollen*.—Abundant; color nearest RHS NN155B.

Calyx: Campanulate; adpressed to corolla; about 7 mm long and about 6 mm across at apex;

Sepals: Five; lanceolate; glabrous adaxial and abaxial; acute apex and fused in basal 2 mm; entire margin; to about 3 mm wide above fusion point and 7 mm long;

Sepal color: Adaxial and abaxial between RHS 137D, RHS 138A and RHS 146B with margins between RHS 145D and RHS 155C;

Fruit: Septicidal capsule; ovoid with acute apex and rounded base; to about 11 mm long and 4 mm across; color with maturity nearest RHS 199C;

Seed: Irregular; flattened, dried; about 2 mm across and about 0.3 mm thick; color nearest RHS N199B;

Hardiness to at least U.S.D.A. zones 4 to 8: The new plant performs best with good drainage and is resistant to drought once established;

Pest and disease resistance: Resistance beyond that typical of Beardtongue plants has not been observed. No other susceptibility or resistance to diseases or pests has been observed except that which is common to *Penstemon*.

It is claimed:

1. A new and distinct cultivar of *Penstemon* plant named 'Pink Pearls' as herein described and illustrated.

* * * * *